United States Patent
Gotman et al.

(10) Patent No.: US 8,712,798 B2
(45) Date of Patent: Apr. 29, 2014

(54) WORKFLOW OPTIMIZATION FOR HIGH THROUGHPUT IMAGING ENVIRONMENTS

(75) Inventors: Shlomo Gotman, Haifa (IL); Shalom Rosenberg, Haifa (IL); Ron Ben-Tal, Nesher (IL); Sethumadavan Sanjay-Gopal, Mayfield, OH (US); Jacob Scott Durgan, Mayfield Heights, OH (US)

(73) Assignee: Koninklijke Philips N.V., Eindhoven (NL)

(*) Notice: Subject to any disclaimer, the term of this patent is extended or adjusted under 35 U.S.C. 154(b) by 1857 days.

(21) Appl. No.: 10/595,990

(22) PCT Filed: Nov. 17, 2004

(86) PCT No.: PCT/IB2004/052469
§ 371 (c)(1),
(2), (4) Date: May 24, 2006

(87) PCT Pub. No.: WO2005/051197
PCT Pub. Date: Jun. 9, 2005

(65) Prior Publication Data
US 2007/0109294 A1    May 17, 2007

Related U.S. Application Data

(60) Provisional application No. 60/525,633, filed on Nov. 26, 2003.

(51) Int. Cl.
*G06Q 10/00* (2012.01)
*G06Q 50/00* (2012.01)
*G06F 19/00* (2011.01)

(52) U.S. Cl.
CPC .................... *G06F 19/321* (2013.01)
USPC .................................................. 705/3; 705/2

(58) Field of Classification Search
CPC combination set(s) only.
See application file for complete search history.

(56) References Cited

U.S. PATENT DOCUMENTS

| | | | | |
|---|---|---|---|---|
| 4,181,347 A | * | 1/1980 | Clark | 378/199 |
| 5,239,591 A | * | 8/1993 | Ranganath | 382/128 |
| 5,452,416 A | * | 9/1995 | Hilton et al. | 715/783 |
| 5,542,003 A | * | 7/1996 | Wofford | 382/132 |
| 5,734,915 A | * | 3/1998 | Roewer | 715/202 |
| 5,963,211 A | * | 10/1999 | Oikawa et al. | 345/424 |
| 5,986,662 A | * | 11/1999 | Argiro et al. | 345/424 |
| 5,988,851 A | | 11/1999 | Gent | |
| 6,004,276 A | * | 12/1999 | Wright et al. | 600/508 |
| 6,047,259 A | | 4/2000 | Campbell et al. | |
| 6,141,398 A | | 10/2000 | He et al. | |

(Continued)

OTHER PUBLICATIONS

Viatronix—3D DICOMM workstations, various web pages 2002-2003.*

(Continued)

*Primary Examiner* — Neal Sereboff (57) ABSTRACT

A medical diagnostic imaging system (10) is coupled to a hospital network (14) to optimize a throughput of a scanner (24). The hospital network includes a hospital records database (18) and a plurality of hospital computers and remote means (20). A workstation (12) is coupled to the scanner (24) and the hospital network (14) and is used to control a scanning process. The workstation (12) includes a display (44), an applications database (52), which is configurable by a user, and an interface means (48) for displaying interactive user interface screens (46) on the display (44). The interface screens (46) allow the user to configure the applications database (52) and interactively control the scanning process.

24 Claims, 11 Drawing Sheets

(56) References Cited

U.S. PATENT DOCUMENTS

| | | | |
|---|---|---|---|
| 6,154,516 A | 11/2000 | Heuscher et al. | |
| 6,185,271 B1 | 2/2001 | Kinsinger | |
| 6,272,469 B1* | 8/2001 | Koritzinsky et al. | 705/2 |
| 6,289,115 B1* | 9/2001 | Takeo | 382/130 |
| 6,306,089 B1* | 10/2001 | Coleman et al. | 600/437 |
| 6,377,831 B1* | 4/2002 | Seshan et al. | 600/407 |
| 6,404,841 B1 | 6/2002 | Pforr et al. | |
| 6,405,191 B1* | 6/2002 | Bhatt et al. | 707/694 |
| 6,411,836 B1 | 6/2002 | Patel et al. | |
| 6,603,494 B1 | 8/2003 | Banks et al. | |
| 6,614,873 B1 | 9/2003 | Taylor et al. | |
| 6,621,917 B1* | 9/2003 | Vilser | 382/128 |
| 6,678,703 B2* | 1/2004 | Rothschild et al. | 1/1 |
| 6,898,302 B1* | 5/2005 | Brummer | 382/131 |
| 7,062,016 B2* | 6/2006 | Kawabuchi | 378/118 |
| 7,073,129 B1* | 7/2006 | Robarts et al. | 715/740 |
| 7,085,804 B2* | 8/2006 | Nolte | 709/201 |
| 7,120,644 B1* | 10/2006 | Canessa et al. | 1/1 |
| 7,127,499 B1* | 10/2006 | Accardi et al. | 709/219 |
| 7,206,462 B1* | 4/2007 | Betke et al. | 382/280 |
| 2002/0016718 A1* | 2/2002 | Rothschild et al. | 705/2 |
| 2002/0060566 A1* | 5/2002 | Debbins et al. | 324/307 |
| 2002/0073429 A1* | 6/2002 | Beane et al. | 725/105 |
| 2002/0085026 A1* | 7/2002 | Bocionek et al. | 345/738 |
| 2002/0146159 A1* | 10/2002 | Nolte | 382/128 |
| 2002/0169636 A1 | 11/2002 | Eggers et al. | |
| 2004/0015079 A1* | 1/2004 | Berger et al. | 600/437 |
| 2004/0029068 A1* | 2/2004 | Sachdeva et al. | 433/24 |
| 2004/0225331 A1* | 11/2004 | Okerlund et al. | 607/14 |
| 2004/0236547 A1* | 11/2004 | Rappaport et al. | 703/2 |
| 2005/0020898 A1* | 1/2005 | Vosniak et al. | 600/407 |
| 2005/0168460 A1* | 8/2005 | Razdan et al. | 345/419 |
| 2005/0206967 A1* | 9/2005 | Viswanth et al. | 358/474 |
| 2005/0228250 A1* | 10/2005 | Bitter et al. | 600/407 |
| 2006/0195564 A1* | 8/2006 | Accardi et al. | 709/223 |

OTHER PUBLICATIONS

Philips Medical EasyVision Conformance Statement 8.2, Jun. 26, 2002.*
Philips Medical EasyVision Conformance Statement 4.3.*
Chooi et al., "Multislice helical CT: the value of muliplanar image reconstruction in assessment of the bronchi and small airways disease" The British Jounal of Radiology, 76 (2003), 536-540.*
Siemens—Magnetom syngo MR Sep. 2003.*
Philips Medical Dicom Conformance Statemetn Jul. 9, 1999.*
Siemens Somatom Volume Zoom Overview A40 Dec. 2001.*
Siemens Somatom Volume Zoom Oct. 2, 2000.*
Agfa MI 0116 102 IMPAX DS3000 Mar. 2002.*
Allen, L.;"Exploiting Database Technology in the Medical Area";1992; IEEE Engineering in Medicine and Biology; pp. 42-49.
Leidner, B.; Standardized whole body computed tomography (SWB-CT)—the use of multi-slice helical CT in blunt multi-trauma patients; http://www.nordictraumarad.com/traumact/Wholebody%20multislice%20CT%202nd%20nordic.pdf.
American College Guideline for the Performance of Computed Tomography (CT) of the Abdomen and Computed Tomography (CT) of the Pelvis; 2002; http://www.acr.org/departments/stand_accred/standards/pdf/ct_abdomen_ct_pelvis.pdf.

* cited by examiner

WORKFLOW OPTIMIZATION FOR HIGH THROUGHPUT IMAGING ENVIRONMENTS

CROSS REFERENCE TO RELATED APPLICATIONS

This application claims the benefit of U.S. provisional application Ser. No. 60/525,633 filed Nov. 26, 2003, which is incorporated herein by reference.

The present invention relates to diagnostic imaging systems and methods. It finds particular application in conjunction with improving the throughput of CT scanners and other diagnostic equipment and will be described with particular reference thereto. However, it is to be appreciated that the invention will also find application in conjunction with improving medical processing efficiency, diagnostic efficiency, and the like.

Multi-slice CT (MSCT) imaging has achieved major technological breakthroughs in a very short period of time. The sixteen slice CT scanner is rapidly becoming the workhorse of the radiology, ET and trauma department. MSCT technology not only enables the acquisition of a large number of CT slices on a routine basis, but also the use of CT to diagnose non-traditional anatomies, e.g. cardiovascular. The advent of multi-slice CT has also opened the possibility of routine CT screening for diagnosing disease at an early, treatable stage.

However, in order for hospitals and imaging centers to fully utilize and tap the power of MSCT, significant workflow bottlenecks need to be overcome. Significant workflow bottlenecks exist in three different areas: (1) patient throughput through the CT scanner, (2) analysis and post-processing of reconstructions numbering more than 1000 images, and (3) storage and archival of CT images.

In a CT scan, the operator first enters the name of the patient, what parameters are needed for the scanning process, including the requested procedure from HIS/RIS, patient's age, patient's weight, requesting physician, scanning with contrast, scanning without contrast, cardiac, etc. After the scanning parameters and patient information are entered, the operator is presented with a large selection of scanning protocols, which come up together on one screen, making the selection of an appropriate scanning protocol a time consuming and difficult task.

Many scans require post processing targeted towards specific disease and/or processes. The permutations and combinations of applications and the distribution of post processing preferences among the physicians is difficult for a clinical department to organize, leading to workflow inefficiencies. The operator manually opens correct post processing application. Currently, some imaging systems open the image processing package associated with the scanner as the scan is running. However, they wait for user input to activate the package and select the images to be produced.

Regarding archival, a paper log is maintained for each patient and each scanner regarding the number of scans, how the scanner is used, and other such information which is very inefficient and time-consuming.

Typically the physicians are requested to make a number of measurements during scans. Currently, the hospital personnel uses a piece of paper with a list of measurement descriptions. To record each measurement the user must take his hand off the mouse/keyboard and write the result down. Moreover, returning to a measurement that it has been already made is not possible and a new measurement must be taken. This all is very time consuming.

To summarize, using current day procedures, hospitals are only able to examine about thirty patients per day with the newest sixteen slice CT scanners. In order to justify the cost of this equipment, the hospitals want to process fifty patients per day.

There is a need for an automated mechanism that will optimize the scanning workflow. The present invention provides a new and improved apparatus and method which overcomes the above-referenced problems and others.

In accordance with one aspect of the present invention, a medical diagnostic image processing system is disclosed. The medical diagnostic image processing system is coupled to a hospital network, which includes a hospital database and a plurality of hospital computers. A scanner acquires images of a patient. A means is coupled to the scanner and the hospital network to control a scanning process, and includes: a display, an applications database which is configurable by a user, and an interface means for displaying interactive user interface screens on the display, which user interface screens allow the user to configure the applications database and interactively control the scanning process by at least activating icons and buttons displayed thereon.

In accordance with another aspect of the present invention, a method of optimizing a throughput of the diagnostic image processing system is disclosed. The medical diagnostic image processing system is coupled to a hospital network, which includes a hospital database and a plurality of hospital computers. Images of a patient are acquired by a scanner. A scanning process is controlled from a workstation which is coupled to the scanner and the hospital network, and includes: a display, an applications database which is configurable by a user, and an interface means. The interface screens are displayed on the display to allow the user to configure the applications database and interactively control the scanning process.

One advantage of the present invention resides in an optimization of scanner's workflow. Other advantages reside in streamlining CT examinations, automating the use of patient information to optimize the scanning protocol, improving patient throughput, and improving operational simplicity of advanced post-processing applications to potentially improve diagnosis.

Another advantage resides in an automation of the workflow that is always visible to the operator.

Another advantage resides in an ease of use.

Another advantage resides in time savings due to the directed workflow.

Another advantage resides in real-time post-processing as the data is acquired permitting the physician to review post-processed images when the patient is still on the table and make a decision whether the patient can be released.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
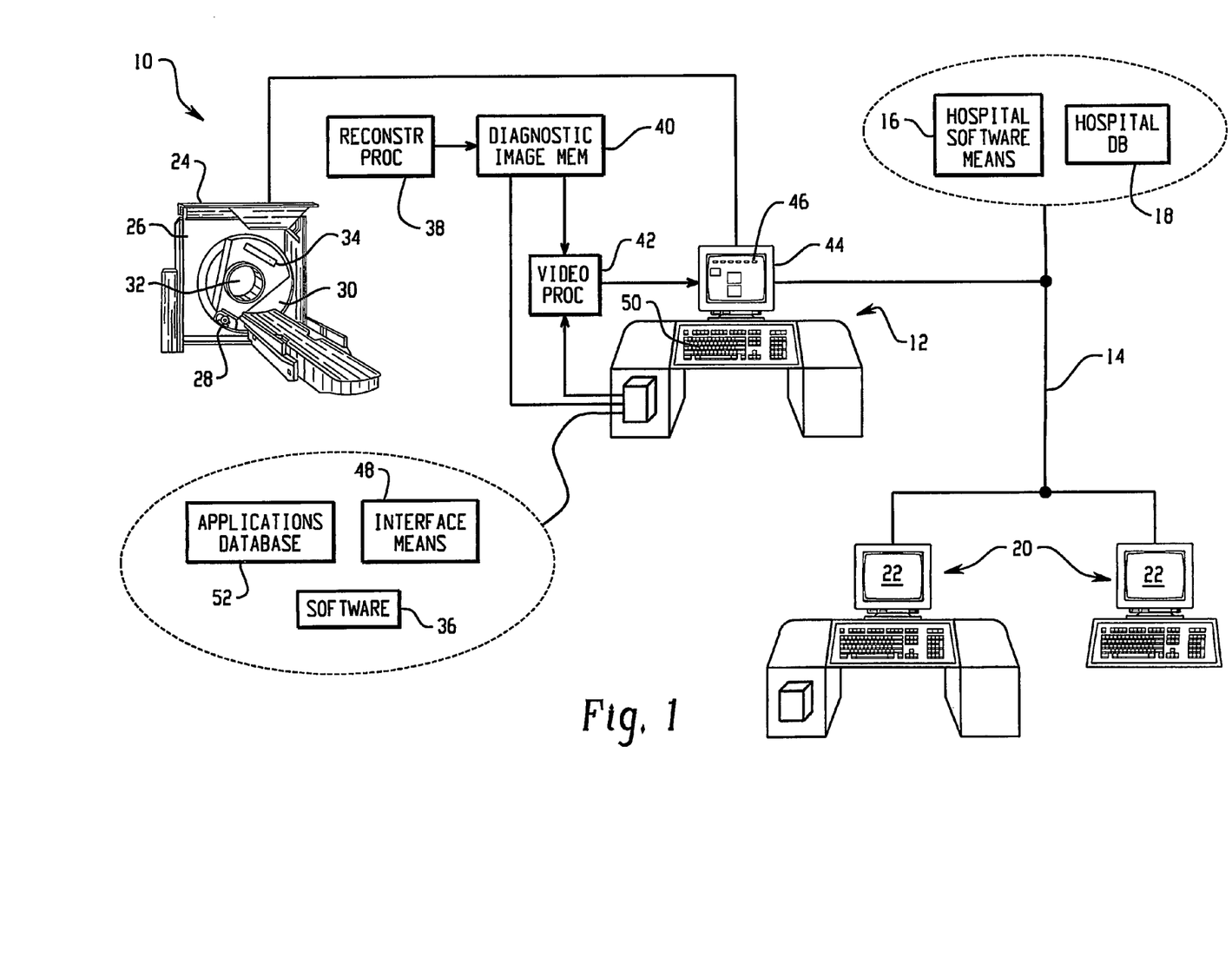
FIG. 1 is a diagrammatic illustration of an imaging system coupled to a hospital network.

With reference to FIG. 1, an operation of an imaging system 10 is controlled from an operator workstation 12 which is coupled to a hospital network 14. The hospital network 14 includes associated software means 16 and a hospital records database 18. The workstation 12 may be hardwired to the network 14 or may communicate with it wirelessly. In this manner, the workstation 12 can communicate with other hospital workstations or computers or remote means 20, which are connected to the hospital network 14, enabling the images and patient records to be forwarded to the appropriate hospital personnel and displayed on associated monitors 22.

Typically, the imaging system 10 includes a CT scanner 24 including a non-rotating gantry 26. An x-ray tube 28 is mounted to a rotating gantry 30. A bore 32 defines an examination region of the CT scanner 24. An array of radiation detectors 34 is disposed on the rotating gantry 30 to receive radiation from the x-ray tube 28 after the x-rays transverse the examination region 32. Alternatively, the array of detectors 34 may be positioned on the non-rotating gantry 26.

Typically, the imaging technician performs a scan using the workstation 12 loaded with software 36. Diagnostic data from the scanner 24 is reconstructed by a reconstruction processor 38 into electronic image representations which are stored in a diagnostic image memory 40. The reconstruction processor 38 may be incorporated into the workstation 12, the scanner 24, or may be a shared resource among a plurality of scanners and workstations. The diagnostic image memory 40 preferably stores a three-dimensional image representation of an examined region of the subject. A video processor 42 converts selected portions of the three-dimensional image representation into appropriate format for display on a video monitor 44. The operator controls the scanning process, production and display of images by using an application interface screen or screens 46 which are incorporated into the workstation 12 and displayed on the monitor 44 to guide the operator through the scanning process. An interface means or processor 48 controls the application interface 46. The operator uses an operator input device, such as a keyboard or mouse 50 to interact with an applications database 52 by navigating the application interface screens 46.

Figure 4:
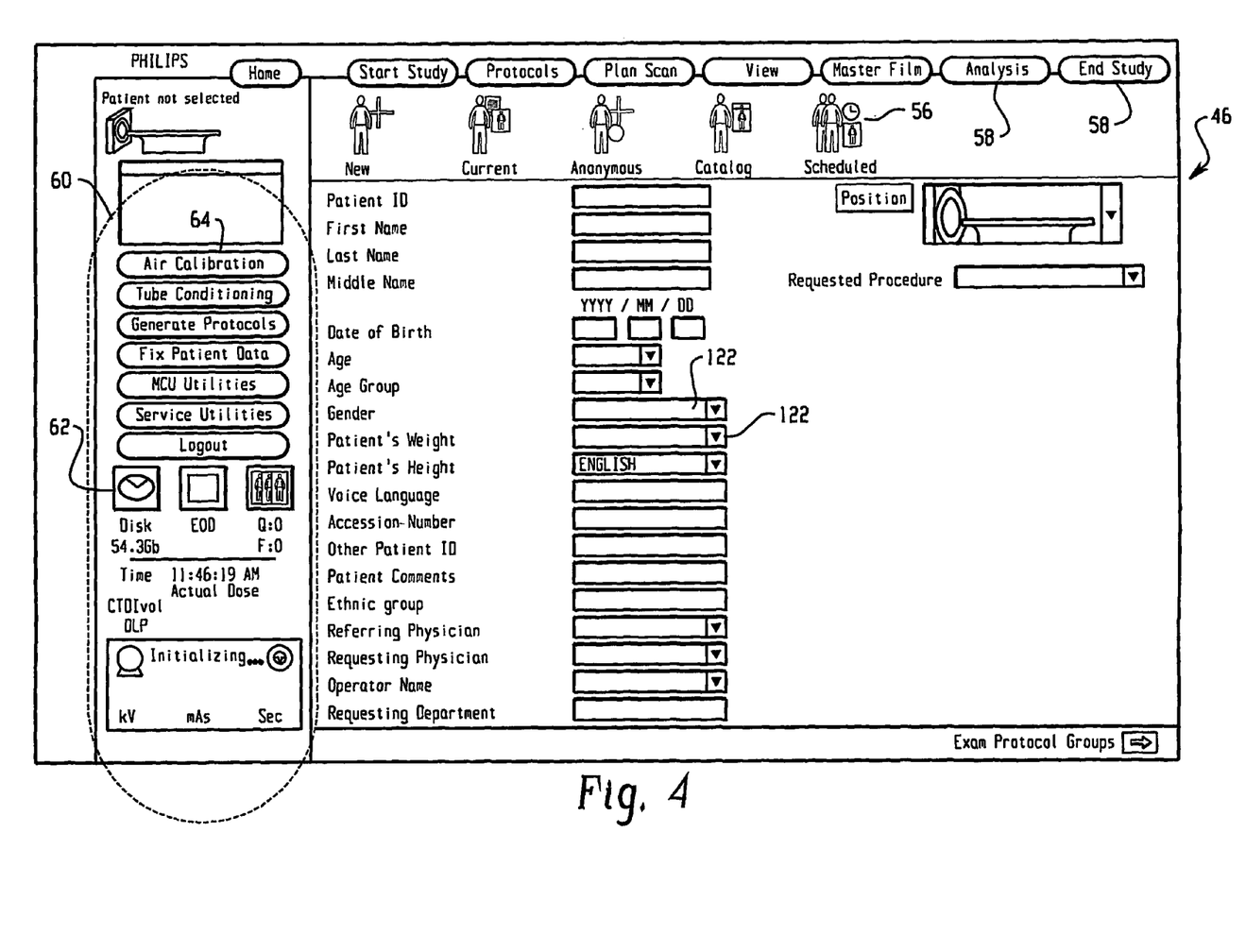
FIG. 4 is a diagrammatic illustration of one interface screen in accordance with the present invention.

With continuing reference to FIG. 1 and further reference to FIG. 4, the interface screen 46 includes a plurality of icons 56 and buttons 58 to navigate through the interface screen(s) 46 and to control scanning workflow. In one embodiment, the screen 46 further includes a scanner home page 60. The scanner home page 60 includes icons 62 and buttons 64 which are used to interactively control the scanner 24.

Figure 3:
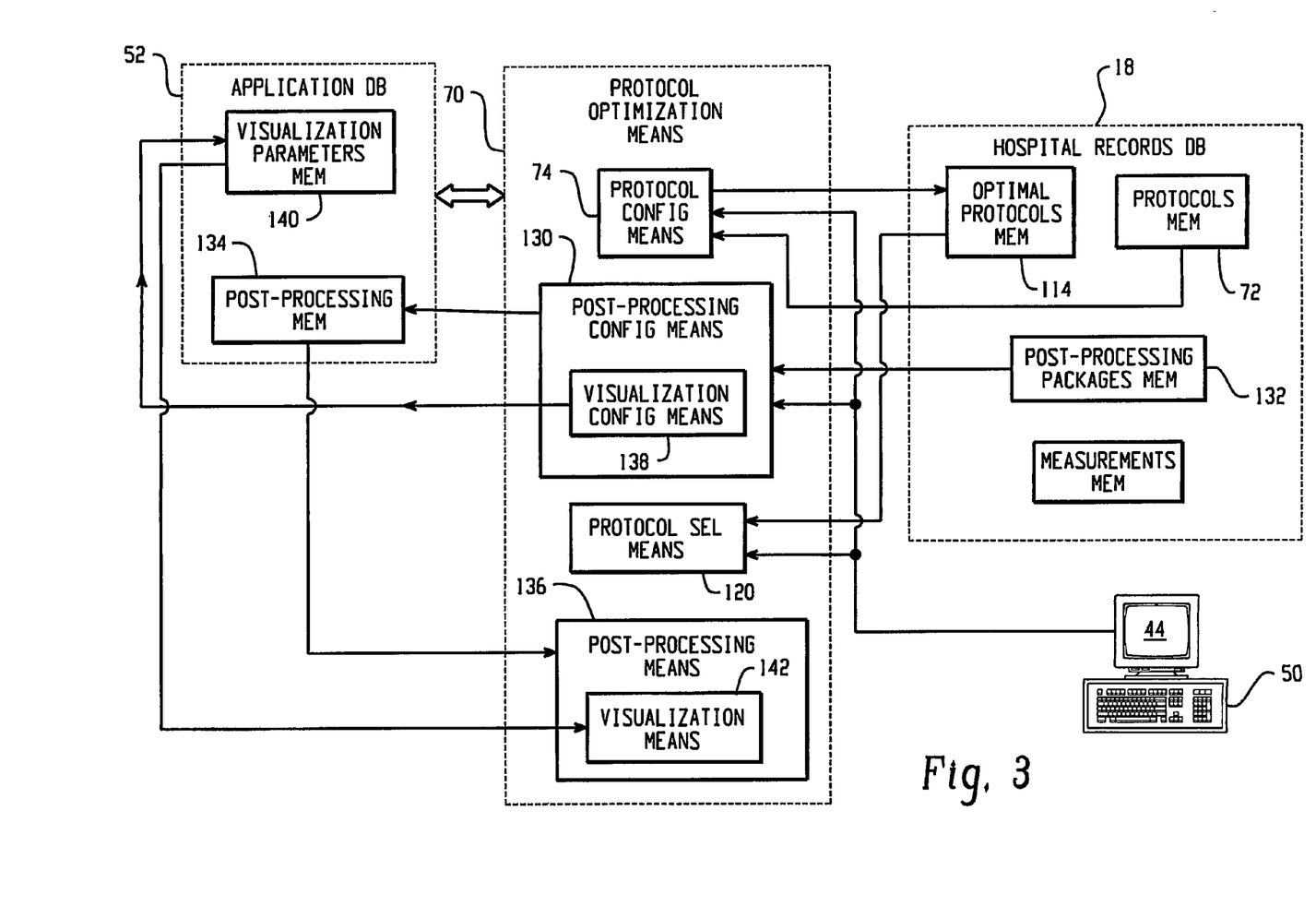
FIG. 3 is a more detailed diagrammatic illustration of some elements of the portion of the imaging system and the hospital network depicted in FIG. 2.

With reference to FIG. 3, a protocol optimization means 70 optimizes selecting a correct exam protocol from a plurality of protocols stored in a protocols memory 72 at the hospital database 18. Generally, there are a number of factors that need to be taken into consideration when choosing the right exam protocol, e.g. the patient's data including patient's age, patient's weight, requesting physician, and scanning parameters including the requested procedure, scanning with contrast, scanning without contrast, which part of the body to scan—cardiac, abdomen, etc.

Figure 5:
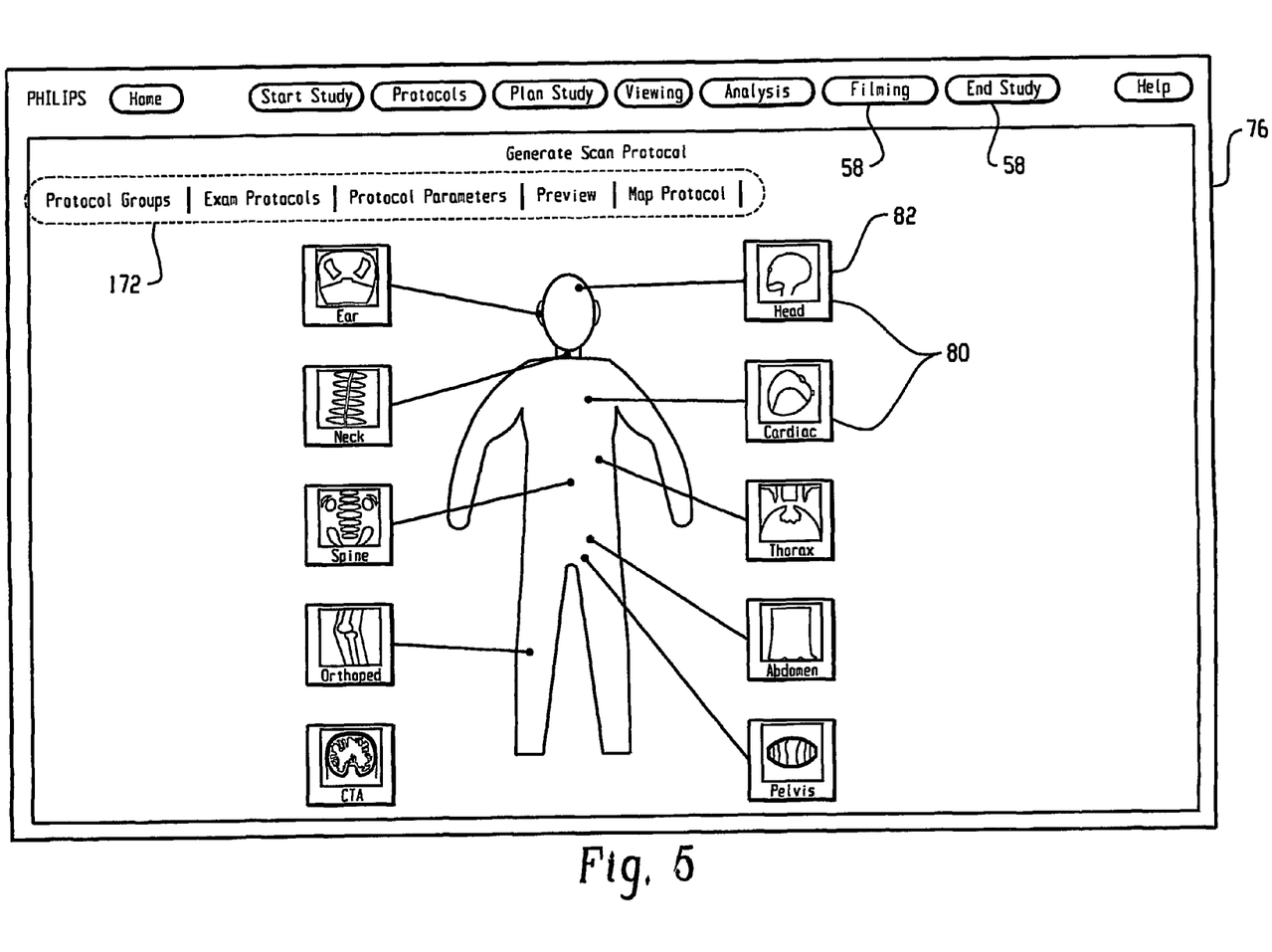
FIG. 5 is a diagrammatic illustration of another interface screen showing protocol groups.
Figure 6:
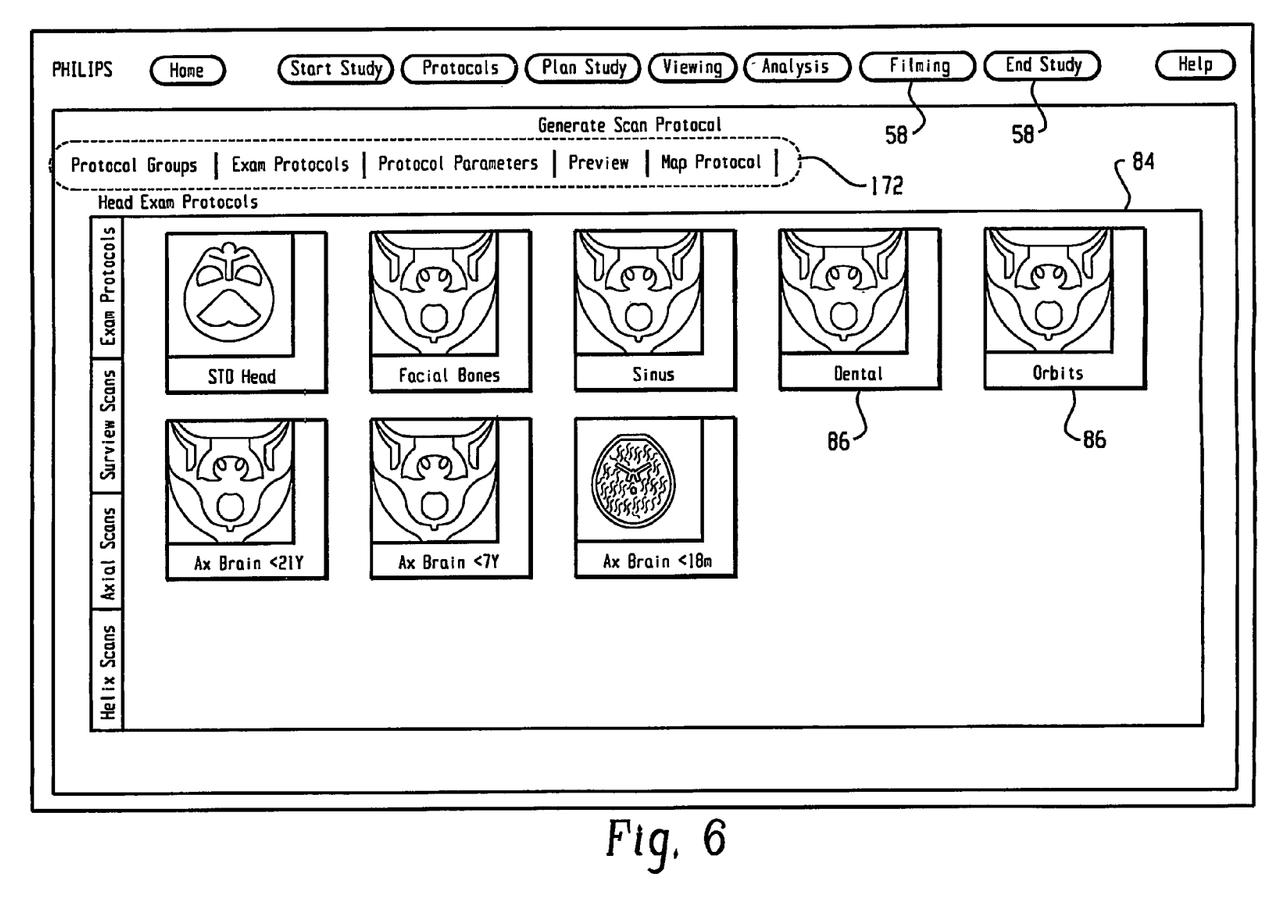
FIG. 6 is a diagrammatic illustration of another interface screen showing selected exam protocols.

With continuing reference to FIG. 3 and further reference to FIGS. 5-6, preferably ahead of time the operator interactively sets up a bank of optimal examination protocols via a protocol configuration means or process 74 which configures optimal protocols by receiving appropriate criteria and optimization parameters supplied by the user. The examination protocols from the protocols memory 72 are displayed on a protocol groups screen 76 as buttons 80 grouped by the examination region, e.g. ear, head, etc., as shown in FIG. 5. When the operator clicks on one of the buttons 80 such as a Head button 82, all protocols available for imaging the head are displayed on a Head Protocol Screen 84, shown in FIG. 6. Head protocols 86 are grouped into examination regions such as sinus, dental, etc. The user chooses one of the existing protocols, e.g. sinus, for further configurations.

Figure 7:
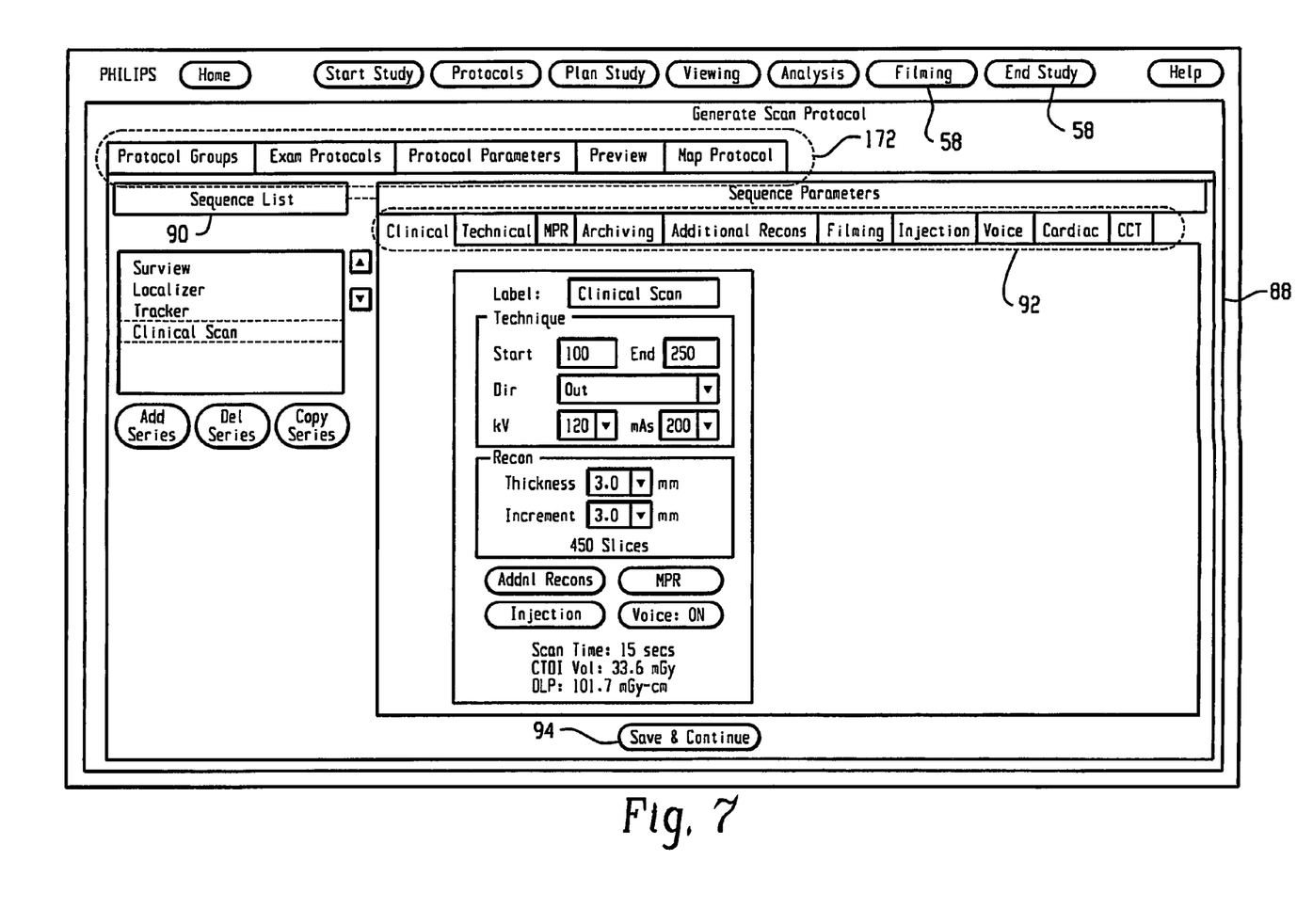
FIG. 7 is a diagrammatic illustration of another interface screen, using which the user can modify protocol parameters.
Figure 8:
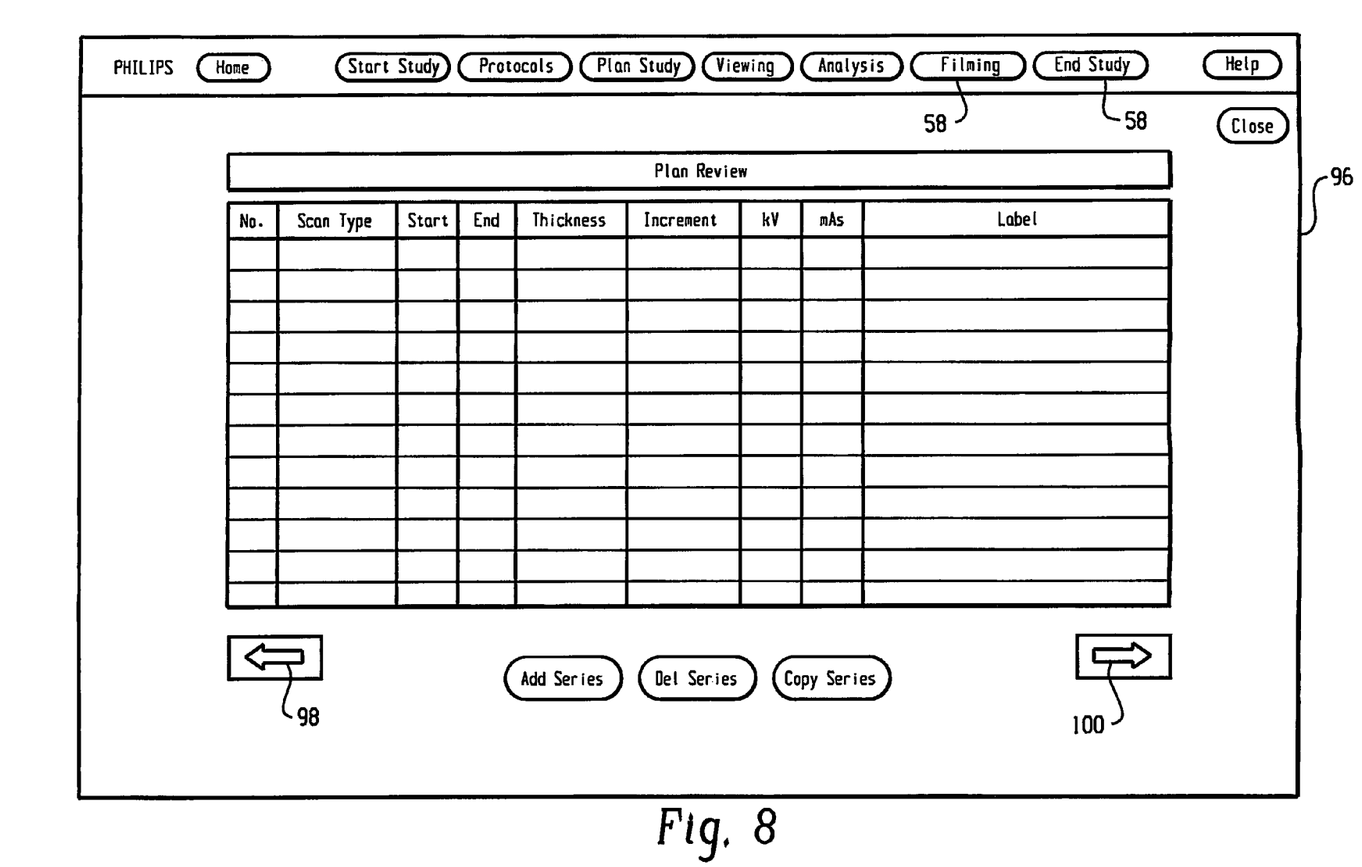
FIG. 8 is a diagrammatic illustration of another interface screen, on which the user can preview created protocol.
Figure 9:
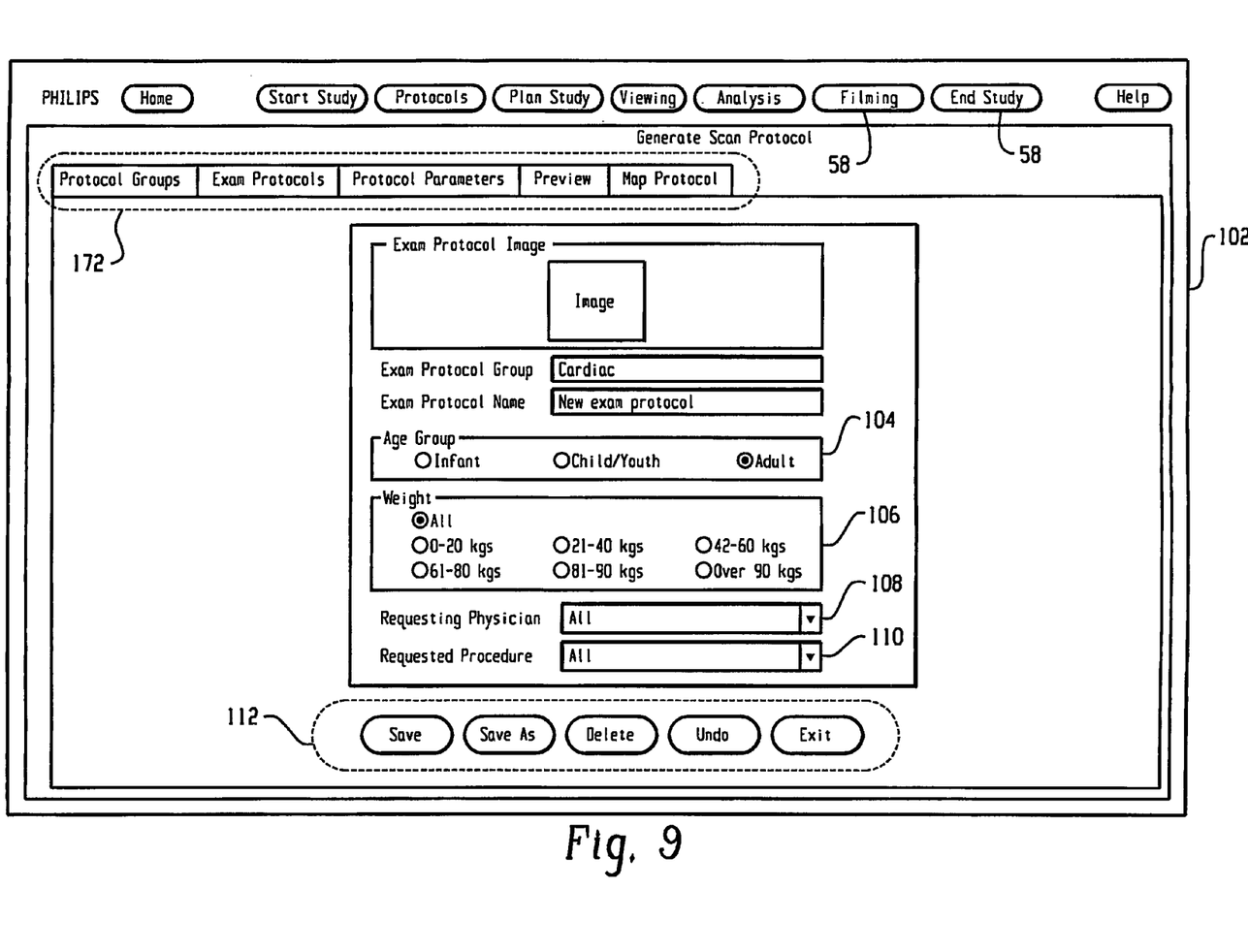
FIG. 9 is a diagrammatic illustration of another interface screen, using which the user maps the protocols.

With reference to FIGS. 7-9, a protocol parameters screen 88 allows the user to enter specific parameters for the chosen protocol, etc. sinus. The user first selects a type of an examination, e.g. clinical scan, by choosing an appropriate entry from a sequence list 90. The user next specifies parameters for selected sequence, e.g. clinical scan, by flipping through tabs 92. The contents of exemplary tabs 92 change based on the selected sequence. The user saves created protocol by clicking on button 94 located on the bottom of the screen 88, and is taken to the next screen, a protocol preview screen 96, shown in FIG. 8. If the created protocol is not to user's satisfaction, the user clicks on a back arrow 98 and is taken back to the protocol parameters screen 88 to make further modifications. If the created protocol is to user's satisfaction, the user clicks on a forward arrow 100 and is taken to the next screen, a map protocol screen 102, shown in FIG. 9 to finish the protocol configuration process. More particularly, the user maps the created protocol to specific patient's groups such as an age group 104, a weight group 106, and the like. The protocols are further mapped to a requesting physician 108 and a requested procedure 110. Of course, further mapping of the protocols into other categories is also contemplated.

With continuing reference to FIG. 9 and reference again to FIG. 3, the user concludes the protocol configuration by using one of buttons 112 located at the bottom of the screen 102. Preferably, the user clicks on a button Save to save the created optimal protocol in an optimal protocols memory 114 at the hospital database 18.

With reference again to FIGS. 3 and 4, a protocol selection means 120 limits a number of scanning protocols available for display by the interface means 48 on the display 44. More specifically, to select the correct exam protocol, prior to each scan, the operator supplies each patient's data and scan parameters, e.g. limiting criteria, by entering the patient data and scanning parameters into the application database 52. The operator types the patient data, e.g. name, weight, requesting physician, requested procedure, etc., into data entry fields 122, shown in FIG. 4. The protocol selection means 120 matches the entered information with the information stored in the optimal protocols memory 114 and determines the nature and region of the scan to be performed, the physician and physician's preferences and scans, and other such information. Preferably, as a result, all unmatched protocols are eliminated, and the interface means 48 displays the most appropriate protocols for scanning the specific patient on the monitor 44. Preferably, the protocol selection means 120 limits the number of protocols between one and three, from which it is quick and easy for the operator to select from.

With continuing reference to FIG. 3, a post-processing configuration means or process 130 allows users to specify their own specific preferences for acquisition and post processing in an interactive manner. The post-processing configuration means 130 matches the users' preferences with post-processing packages which are stored in a post-processing packages memory 132 at the hospital database 18. Generally, many examination procedures require standard post-processing, e.g. the spine scanning usually requires MPR, the cardiac study is typically displayed in Cardiac Review package, the dental scans are typically displayed in the Dental application, etc. Some physicians routinely request filming as a part of the post-processing process that might be set up during the post-processing configuration process 130. Preferably, the user sets up the MPR as a standard post-processing for all spine exams, Cardiac Review package as a standard post-processing for all cardiac exams, filming for specific examinations or requesting physicians, etc. Configured post-processing packages are stored in a post-processing memory or database 134 residing on the workstation 12. Alternatively, the configured post-processing packages are stored in a database residing on the scanner 24.

A post-processing means 136 searches the post-processing memory or database 134 for the post-processing package that matches type of scan and other parameters entered by the operator into the data entry fields 122. The post-processing package is started automatically to generate post-processed images and film as the data is acquired; e.g., the cardiac study is displayed in Cardiac Review package automatically, every spine examination is displayed automatically in real-time MPR, the Dental application is launched automatically for a dental examination, etc. The physician reviews post-processed images when the patient is still on the table and makes a decision whether the patient can be released. Preferably, the images and other data are automatically sent wherever it needs to go, e.g. to the reviewing physician's workstation.

With continuing reference to FIG. 3, the post-processing configuration means 130 includes a visualization configuration means 138. Preferably, for the study of the specific region, e.g. abdomen, the visualization configuration means 138 determines the optimal screen layout, the rendering mode for each viewport, the specific parameters for each viewport (e.g., classification for volume rendering), the display orientation, image zoom/pan, the slab thickness, restriction of volumes of interest, filming, storage, and report parameters. Furthermore, preferably, in determining the level and zoom, slice and slab thicknesses, windowing, and the like, the visualization configuration means 138 takes into consideration the preferences of each requesting physician. Visualization parameters are stored in a visualization parameters memory or database 140. A visualization means 142 automatically displays the images on the screen with the right zoom, right filter, right report parameters, etc., based on the data entered by the operator for a specific patient. The physician is able to review the images very quickly without the need to reconstruct again the region of examination and/or film right away with right zoom, filter, etc.

With reference again to FIG. 2, a parameters optimization means 150 automatically optimizes various scan parameters such as the kV and mA for the protocol selected by the protocol selection means 120, saving the operator the time to make these selections depending on clinical study. Preferably, the optimization criteria includes scanning mode, scan duration, patient dose, required image quality, etc. In one embodiment, the patient doze might be optimized depending on where the radiation is coming from, e.g. from the side or other direction, according to the size of the patient, the region of the scan, clinical study, e.g. trauma, required image quality, etc.

Figure 2:
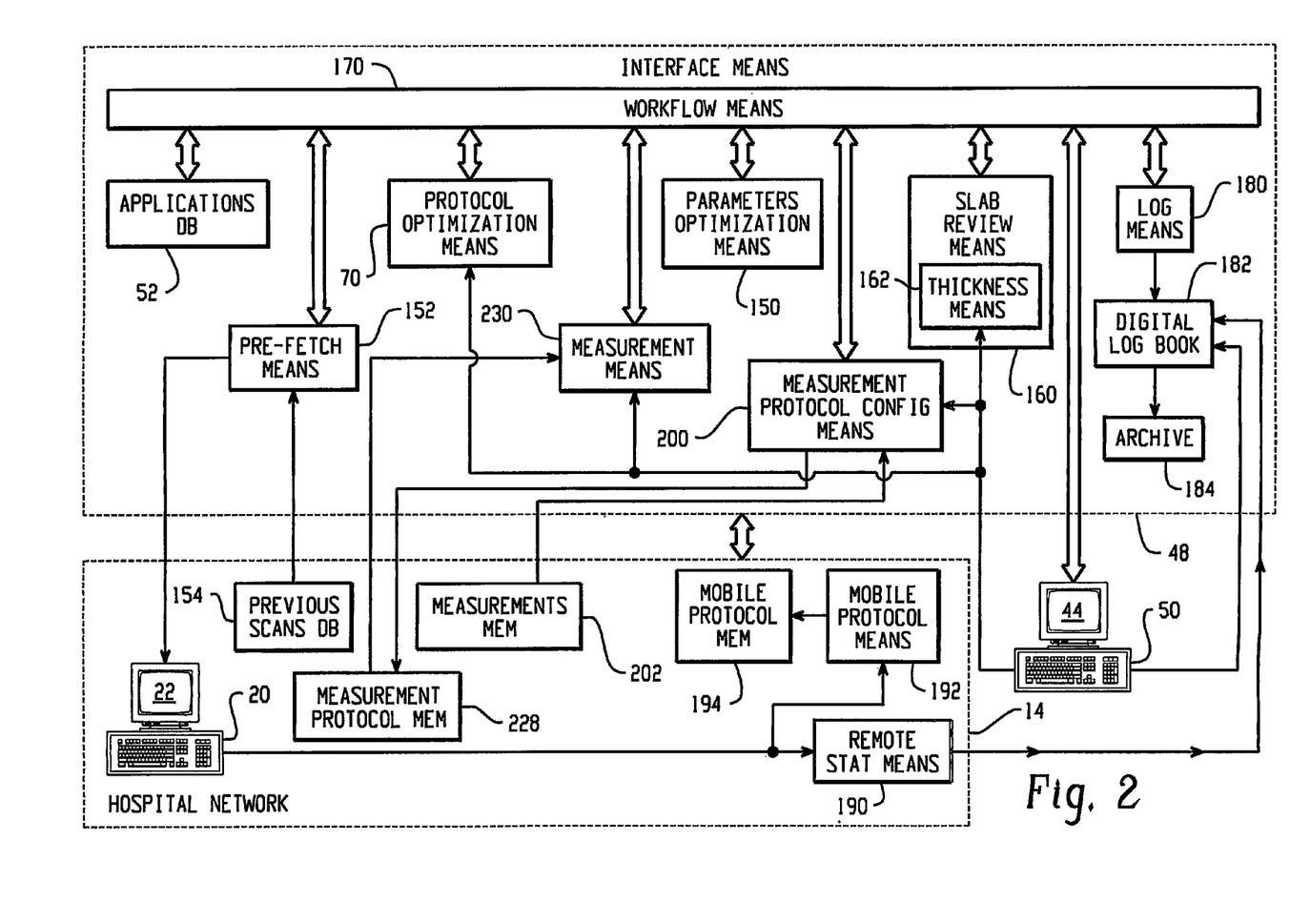
FIG. 2 is a diagrammatic illustration of a portion of the imaging system including coupled to a hospital network.

With continuing reference to FIG. 2, a pre-fetch means 152 searches a previous scan database 154 residing at the hospital database 18 for earlier scans of the same patient. The pre-fetch means 152 retrieves previous scans, which have been stored from previous exams from the same or different modality, into the workstation on which the physician examines the current scans of the patient. Preferably, the pre-fetch means 152 performs pre-fetch of the previous scans automatically when the patient data is entered by the operator at the beginning of the exam, without waiting for the previous scans to be requested. Preferably, the earlier images are directly sent to the physician's workstation and registered by using one of known pre-registration techniques to display earlier and current scans side by side on the monitor 22. Alternatively, the earlier images are directly sent to the physician's workstation only if requested by the reviewing physician.

Preferably, the pre-fetch means 152 determines if there are earlier related scans, e.g., whether the current examination is one of a series of follow-up examinations, and determines the parameters and protocols used in the previous scans. The previously used parameters and protocols are offered to the operator to be used in conjunction with the protocol selection and parameter optimizing steps. The operator reviews what parameters were entered when the patient was previously scanned, e.g. age, weight, etc. Preferably, the operator uses the same parameters or, as an alternative, the operator adjusts the previously entered parameters. Use of the same parameters for the new study is very useful for routine exams, e.g. lungs scan, since it is desirable to perform the routine exams in the same way as it was done few years ago.

With continuing reference to FIG. 2, a slab review means 160 merges groups of slices into thicker slabs so that fewer slabs need to be examined. Preferably, the operator interactively supplies a thickness of the slab to a thickness determining means 162 to view slices in slabs of the selected thickness. The operator reviews slabs with an adjustable speed in any direction. If any slab shows features of interest, it is interactively separated by the operator back into its component slices in real-time. Preferably, the slab review means 160 provides real-time navigation in axial/coronal/sagittal and any general direction through the volume using variable-thickness slab with MPR/MIP/3D/4D rendering.

A streamlined directed workflow or workflow means or process 170 integrates all functional components of the interface means 48. The workflow means 170 leads the operator through the scanning process by presenting to the operator step by step process for applications and providing for quick, easy scan set up, scan acquisition, and scan completion. In one embodiment, illustrated in FIGS. 5-9, the workflow means 170 leads the operator through generating a new protocol by a use of tabs 172 positioned in a specific logical order, buttons such as the Save button 94 of FIG. 7, and the like.

A log means 180 receives the patient and scan information and writes the information into a digital log book 182. The digital log book 182 is stored at the interface means 48 for each patient and each scanner regarding the number of scans, how the scanner is used, and other such information. The log means 180 selects which information needs to be archived into an archive 184. Preferably, if a paper copy is to be stored, the log means 180 initiates printing the information stored in the digital log book 182 in a regular intervals in the format to which the hospital personnel is accustomed to.

A remote statistics means 190 enables the remote access of the scanner 24 from the remote means 20 for optimizing scanner usage and increasing patient throughput. In addition, it enables statistical analysis of the scanners for planning and budgeting purposes. The user initiates mining of the digital log book 182 to find out more about how the scanner is used and determine how yet greater efficiencies can be achieved. Preferably, hospital administrators can estimate and optimize scanner usage, distribute patient load between two or more scanners in a multi-scanner environment, and the like.

A mobile protocol means 192 allows the physician or others to remotely specify and preload the selected scan protocols by using the remote means 20 such as PDA, computer, the web, or the like, into the hospital network system 14. Preloaded protocols are stored in a mobile protocols memory 194. The interface means 48 automatically uploads the information for each patient to the CT scanner 24, eliminating the operator protocol selection step. Alternatively, the information is uploaded directly to the CT scanner.

A measurement protocol configuration means 200 configures a work list of measurements. Often, as a part of an imaging examination, the physician needs to have measurements based off the centerline and cut planes along a vessel (or group of vessels), which are normal to the centerline.

Figure 10:
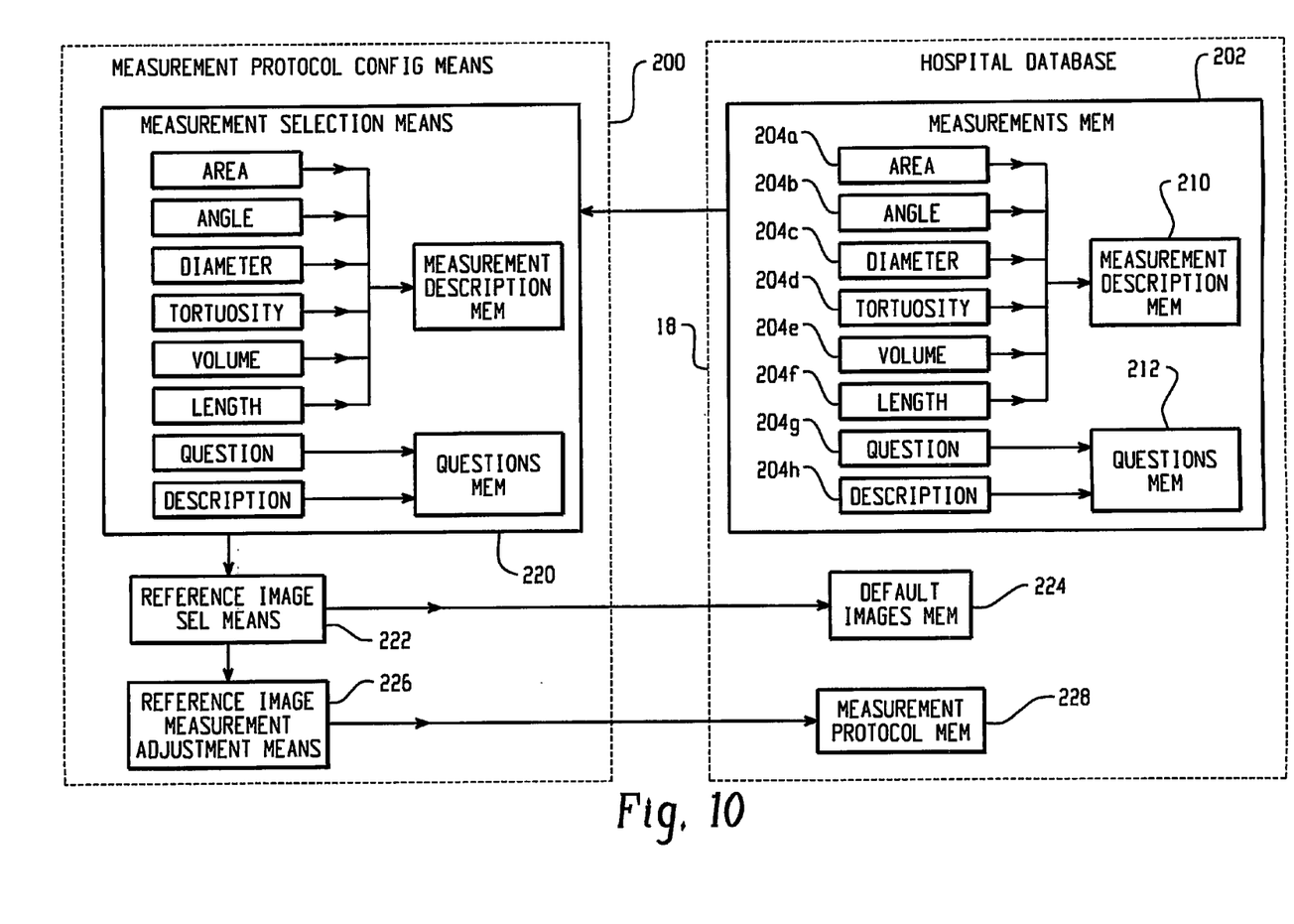
FIG. 10 is a more detailed diagrammatic illustration of some elements of the portion of the imaging system and the hospital network depicted in FIG. 2.

With continuing reference to FIG. 2 and further reference to FIG. 10, measurements, which can be performed by using the imaging system 10, are stored in a measurement database or memory 202 residing at the hospital database 18 and typically include the following exemplary measurements:

(a) Area Measurement 204*a* which is a measurement of an area of a cut plane at a specific place along the centerline;

(b) Angle Measurement 204*b* which is a measurement of an angle between three points along the centerline;

(c) Diameter Measurement 204*c* which is a measurement of a diameter of the vessel on a cut plane at a specific point along the centerline;

(d) Tortuosity Measurement 204*d* which is a measurement defined with two or three points along the centerline to specify the amount of twist in the vessel;

(e) Volume Measurement 204*e* which is a measurement defined with two cut planes along the centerline of the vessel;

(f) Length Measurement 204*f* which is a measurement of a distance along the centerline between two points on the centerline;

(g) Question Asked 204*g* which a question that the user is requested to answer;

(h) Description Needed 204*h* which is a question that the operator might asked that takes a few words to answer.

A measurement description memory or database 210 includes a description for each measurement category 204*a-f* which each is linked to each measurement category to help the user in setting up and making the measurement. A question memory 212 includes a list of answers, empty data entry fields, and the like which are linked to the Question 204*g* and Description 204*h* categories to help the user in answering questions asked.

The user interactively selects the measurements from the measurements database 202 via a measurements selection means 220. For a specific measurement protocol, all of the available measurements might be selected or only a part of the available measurements might be selected from the measurements database 202. A reference image selection means 222 selects: a reference image showing an example vessel of which the measurements are to be made on. A plurality of default reference images is stored in a default image memory 224 at the hospital database 18. Preferably, correct reference image is displayed automatically in response to the user's selection of the measurements. Alternatively, the user interactively chooses one of the reference images that is more to his/her liking. The reference image is displayed on the monitor 44 providing a visual indication of where each individual measurement is placed. Preferably, each measurement is linked to a different marker and only the current measurement appears on the reference image. The user interactively provides an input to a reference image measurement adjustment means 226 by adjusting the measurement marker in the displayed reference image. Configured measurement protocols are stored in a measurements protocols memory 228.

Figure 11:
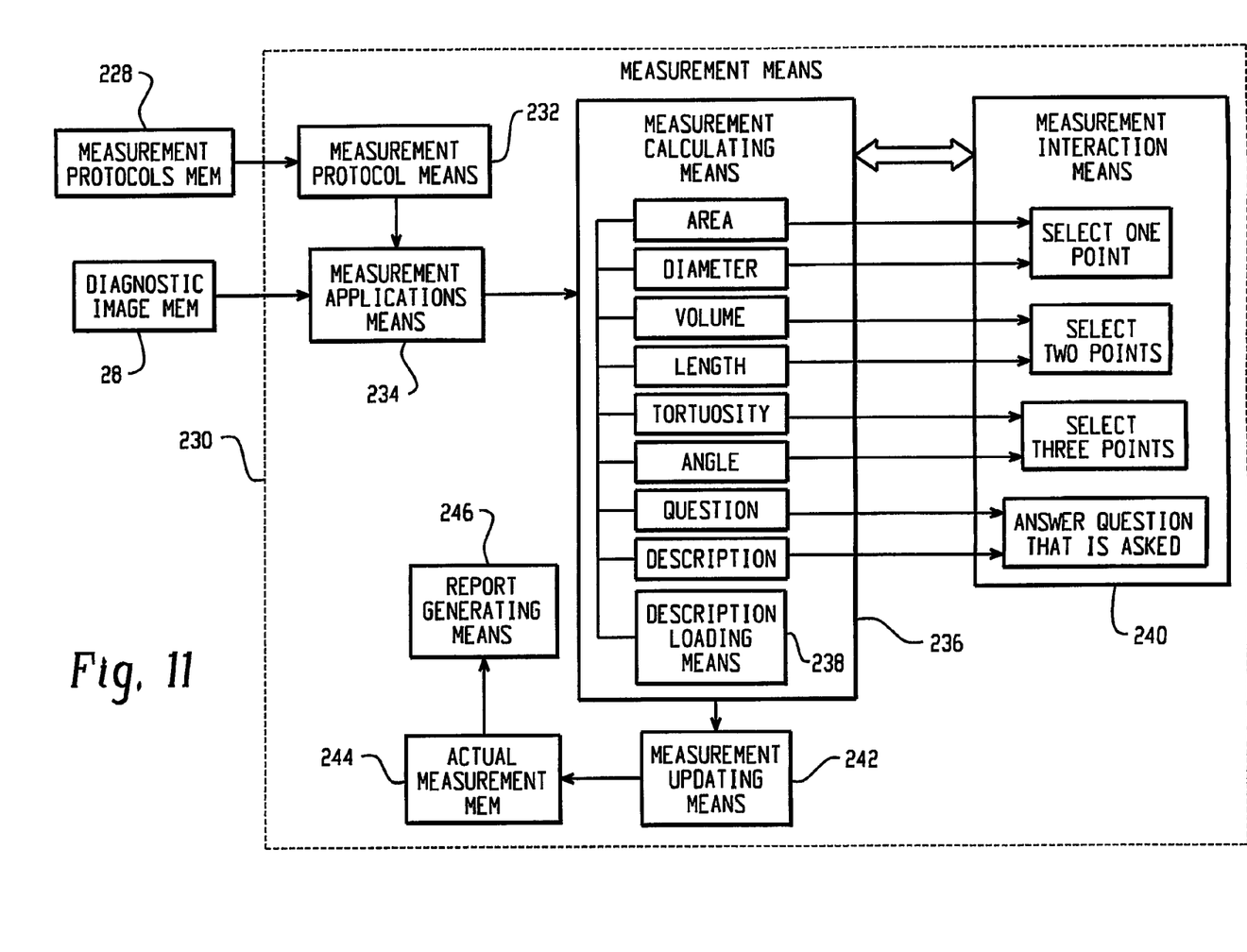
FIG. 11 is a more detailed diagrammatic illustration of some elements of the portion of the imaging system and the hospital network depicted in FIG. 2.

With reference to FIG. 11, a measurement means 230 performs actual measurements. A measurement protocol means 232 automatically selects the correct measurement protocol based on the operator data entries. A measurement application means 234 extracts the centerline, normal cut planes within a vessel, and the like from the patient's image using one of known measurement application packages. A measurement calculating means 236 performs the actual measurements by retrieving measurements configured in the selected protocol. A description loading means 238 loads linked measurement description and/or corresponding answers/data entry fields for each measurement category 204*a-h*. The monitor's screen automatically changes for each measurement. A measurement interaction means 240 accepts the entry from the operator to adjust actual measurements, e.g. change the number of points along the centerline, etc. A measurements updating means 242 automatically updates the measurements to the value which is shown on the screen is showing. The updated measurements are stored in an actual measurements memory 244. When all the measurements for the selected protocol are completed, the operator preferably prints out the entire list of measurements into a report via a report generating means 246.

The invention has been described with reference to the preferred embodiments. Modifications and alterations may occur to others upon a reading and understanding of the preceding detailed description. It is intended that the invention be constructed as including all such modifications and alterations insofar as they come within the scope of the appended claims or the equivalents thereof.

Having thus described the preferred embodiments, the invention is now claimed to be:

1. A medical diagnostic imaging system for acquiring images of a patient, the imaging system being coupled to a hospital network which hospital network includes a hospital database which stores patient data including patient images, and a plurality of hospital computers, the imaging system comprising:

a scanner which scans the patient using a selected examination protocol to generate image data;

a scanner control which controls the scanner, the scanner control being coupled to the scanner and the hospital network;

a display, an applications database which is configurable by a user;

an examination protocol database which stores a plurality of examination protocols;

an interface which causes the display to display interactive user interface screens on the display, which user interface screens allow the user to configure the applications database, enter a patient's limiting parameters, select from the plurality of selectable examination protocols, and interactively control the scanner by activating icons and buttons displayed thereon;

a computer to:
receive the patient's limiting parameters and a nature and region of a scan by any one of:
entered by the user into data entry fields displayed on the user interface screens,
from the hospital database, or
from a remote terminal;
match the received patient's limiting parameters and the nature and region of the scan with information stored in the examination protocol database to reduce the plurality of selectable examination protocols to a smaller, reduced set of examination protocols;
control the display to display the reduced examination protocol set;
receive an input indicative of a selected examination protocol of the displayed reduced examination protocol set;
control the scanner control such that the scanner control controls the scanner to perform the selected examination protocol which generates scan data;
a post-processor configured to reconstruct the scan data into diagnostic images, format the reconstructed diagnostic images, and control the display to display the reconstructed diagnostic images.

2. The system as set forth in claim 1, wherein the post-processor is further configured to:
automatically selects and commence post-processing during data acquisition with one of a plurality of post processing techniques in accordance with types and formats of images commonly generated with the selected examination protocol, or patient's limiting parameters entered by the user into data entry fields to generate patient images.

3. The system as set forth in claim 2, wherein the computer is further configured to:
search the hospital database for previous diagnostic images of the patient, retrieve the previous images, and automatically send the previous images to a diagnosing physician's hospital computer without a transfer request from the physician.

4. The system as set forth in claim 3, wherein the computer is further configured to:
retrieve one of the examination protocols from the hospital database that was used to generate the previous images of the patient.

5. The system as set forth in claim 3, wherein the diagnostic images generated using the selected examination protocol are generated by a different imaging modality than the previous images and wherein the computer is further configured to automatically register and control the display to display the previous and current diagnostic images at the physician's computer.

6. The system as set forth in claim 1, wherein the post processor is further configured to:
retrieve from the hospital database visualization parameter preferences of a diagnosing radiologist and adjust level, zoom, slice and slab thickness, windowing, and other visualization parameters in accordance with the diagnosing radiologist's preferences retrieved from the hospital database.

7. The system as set forth in claim 1, wherein the scanner includes a CT scanner; and
the interface further includes:
a processor configured to automatically select optimization parameters of an x-ray source of the CT scanner based on the selected examination protocol, the optimization parameters including:
voltage supplied to the CT scanner x-ray source,
amperage supplied to the CT scanner x-ray source, and
an x-ray dose supplied to the patient.

8. The system as set forth in claim 1, wherein the computer is further configured to:
merge groups of individual image slices into slabs of a plural number of slices;
control the display to display the slabs; and
receive a designation of one of the slabs;
separate the designated one of the slabs into its constituent individual image slices and control the display to display the constituent individual image slices.

9. The system as set forth in claim 1, wherein the computer is further configured to:
assemble the entered patient's limiting parameters, scanner running time, examination protocols used and other scan information for each scanned patient, and generate a digital log book.

10. The system as set forth in claim 9, further including:
a remote processor configured to remotely access and mine the digital log book to provide statistical analysis for optimizing scanner use.

11. The system as set forth in claim 1, further including:
a remote, portable computer; and
wherein the interface is configured to automatically upload the selected examination protocol from the remote portable computer.

12. The system as set forth in claim 1, wherein the patient's limiting parameters include patient size, patient age, a radiologist identification, radiologist preferences, and a nature and region of the patient to be scanned.

13. A method of optimizing a throughput of a diagnostic image processing system, comprising the steps of:
storing a plurality of the examination protocols in an application database in a hospital network;
with one or more computers, receive patient limiting parameters of a patient to be imaged matching patient limiting parameters with the examination protocols stored in the application database, and selecting a limited number of the examination protocols based on the matching;
displaying a list of the limited number of the examination protocols on a display;
receiving an input indicating a selected one of the limited number of examination protocols;
sending instructions to the diagnostic imaging system to performing a diagnostic imaging scan of the patient using the selected examination protocol to generate image data;
reconstructing the generated image data into a diagnostic image; and
displaying the diagnostic image on the display.

14. A medical diagnostic imaging system coupled to a hospital network, wherein the hospital network interconnects a hospital archive database, computers, computer displays, and a diagnostic scanner which scans a patient using a selected examination protocol selected from a plurality of examination protocols stored in an examination protocol database, the medical diagnostic imaging system including:
a display device; and
a one or more computer programmed to:
match patient size, patient age, radiologist identification, radiologist preferences, and a nature and region of the patient to be scanned from the hospital archive database and/or entered by a clinician with the examination protocols stored in the examination protocol database to select a fraction of the plural examination protocols;

generate an operator interactive display on the display device a menu of the fraction of the plurality of examination protocols;

receive an input indicative of a selected one of the limited number of examination protocols on the displayed menu;

implement the selected one of the examination protocols.

15. The medical diagnostic imaging system as set forth in claim 14, wherein the computer is further programmed to:

while the scanner is implementing the selected protocol to acquire image data, automatically, without user instructions, commence post-processing during the image data acquisition in accordance with a type and format of images most commonly generated for the selected examination protocol.

16. The medical diagnostic imaging system as set forth in claim 14, wherein the scanner is a CT scanner and the computer is further programmed to:

control the CT scanner to set a tube voltage and a tube current for an x-ray source of the CT scanner in accordance with the selected examination protocol.

17. The medical diagnostic imaging system as set forth in claim 14, wherein the computer is further programmed to:

search the hospital archive database for archive images of the patient currently undergoing examination and route the archive images directly to a display terminal of a diagnosing radiologist, automatically without a transfer request.

18. The medical diagnostic imaging system as set forth in claim 14, wherein the computer is further programmed to:

search the hospital archive database to determine if a current scan is a follow-up scan, determine parameters and examination protocols used in prior scans, and set the scanner to conduct the current examination using the same parameters and examination protocol used in the prior scans.

19. The medical diagnostic imaging system as set forth in claim 14, wherein the computer is further programmed to:

search the hospital archive database to determine preferences of a diagnosing radiologist and adjust level, zoom, slice and slab thicknesses, windowing, and other display characteristics in accordance with the retrieved preferences of the diagnosing radiologist.

20. The medical diagnostic imaging system as set forth in claim 14, wherein the computer is further programmed to:

merge groups of slice images into a smaller number of slab images, display the slab images on the display, and display on the display the individual slice images corresponding to each slab image designated by a diagnosing radiologist.

21. The medical diagnostic imaging system as set forth in claim 14, wherein the computer is further programmed to:

generate a series of prompts to an operator to lead the operator sequentially through an imaging procedure.

22. The medical diagnostic imaging system as set forth in claim 14, wherein the computer is further programmed to:

for each scanner, automatically generate a digital log book by collecting entered patient information and scan information for each patient examined by the corresponding scanner.

23. The medical diagnostic imaging system as set forth in claim 14, wherein the computer is further programmed to:

at the beginning of a scan procedure, automatically upload examination protocol information previously submitted from a remote computer or PDA.

24. The medical diagnostic imaging system as set forth in claim 14, wherein the computer is further programmed to:

automatically commence post-processing during data acquisition in accordance with types and formats of images most commonly generated for the selected examination protocol; and search the hospital archive database for images of the patient currently undergoing examination and routing the archive patient images directly to a display terminal of a diagnosing radiologist, automatically without a transfer request; and search the hospital archive database to determine if a current scan is a follow-up scan, determine parameters and examination protocols used in prior scans, and set the scanner to conduct the follow-up examination using the same parameters and examination protocols; and search the hospital archive database to determine preferences of a diagnosing radiologist and adjust level, zoom, slice and slab thicknesses, windowing, and or other display characteristics in accordance with the retrieved preferences of the diagnosing radiologist; and generate a series of prompts to an operator to lead the operator sequentially through an imaging procedure; and for each scanner, automatically generate a digital log book by collecting entered patient information and scan information for each patient examined by the corresponding scanner; and at the beginning of a scan procedure, automatically uploading examination protocol information previously submitted from a remote computer or PDA.

* * * * *